(12) United States Patent
Mann et al.

(10) Patent No.: US 8,268,747 B2
(45) Date of Patent: Sep. 18, 2012

(54) SAFENING PENOXSULAM HERBICIDE INJURY IN WATER-SEEDED, DIRECT-SEEDED AND TRANSPLANTED PADDY RICE

(75) Inventors: Richard K. Mann, Franklin, IN (US); Deborah G. Shatley, Lincoln, CA (US)

(73) Assignee: Dow AgroSciences, LLC., Indianapolis, IN (US)

( * ) Notice: Subject to any disclaimer, the term of this patent is extended or adjusted under 35 U.S.C. 154(b) by 54 days.

(21) Appl. No.: 12/767,107

(22) Filed: Apr. 26, 2010

(65) Prior Publication Data

US 2010/0279864 A1 Nov. 4, 2010

Related U.S. Application Data

(60) Provisional application No. 61/174,627, filed on May 1, 2009.

(51) Int. Cl.
*A01N 25/32* (2006.01)

(52) U.S. Cl. .................................. 504/106; 504/104

(58) Field of Classification Search .................. 504/106, 504/104
See application file for complete search history.

(56) References Cited

FOREIGN PATENT DOCUMENTS

WO PCT/US2010/032357 4/2010
WO WO 2010/126812 11/2011

OTHER PUBLICATIONS

Ottis, B.V., Rice Weed Control with Penoxsulam (Grasp), 2003, B.R. Wells Rice Research Studies-2003, 144-150.*
Willingham, S D; Falkenberg N R; McCauley G N; Chandler J M: "Early Postemergence Clomazone Tank Mixes on Coarse-Textured Soils in Rice" Weed Technology, vol. 22, No. 4, Oct. 2008,—Dec. 2008 pp. 565-570, XP002586989 ISSN: 0890-037X DOI: 10.164/WT-08-151.1 table 2.

* cited by examiner

*Primary Examiner* — Johann Richter
*Assistant Examiner* — Andriae M Holt
(74) *Attorney, Agent, or Firm* — Robert Chang

(57) ABSTRACT

Clomazone safens rice from the slight amounts of damage caused by penoxsulam at concentrations required to adequately control undesirable vegetation.

2 Claims, No Drawings

SAFENING PENOXSULAM HERBICIDE INJURY IN WATER-SEEDED, DIRECT-SEEDED AND TRANSPLANTED PADDY RICE

FIELD OF THE INVENTION

This invention concerns the safening of the herbicidal injury caused by penoxsulam (2-(2,2-difluoroethoxy)-N-(5,8-dimethoxy[1,2,4]triazolo[1,5-c]pyrimidin-2-yl)-6-(trifluoromethyl)benzenesulfonamide) in water-seeded, direct-seeded and transplanted paddy rice.

BACKGROUND OF THE INVENTION

When agrochemicals, such as plant protection agents and especially herbicides, are used, the cultivated plants may be damaged to a certain degree, depending on factors such as the dose of agrochemicals, the timing of the application of the herbicides relative to the crop stage, their method of application, the species of cultivated plant, the nature of the soil and climatic conditions, for example, length of time of exposure to light, temperature and amounts of precipitation. Thus, it is known that cultivated plants which are to be protected from the adverse effect of undesirable plant growth may be damaged to a certain degree when an effective dose of herbicide is used. Various substances, which are capable of specifically preventing the adverse effect of an herbicide on the cultivated plants, i.e., of protecting the cultivated plants without at the same time noticeably influencing the herbicidal action on weeds to be combated, have been proposed to solve this problem. However, it has been found that the antidotes proposed frequently have only a narrow field of use, i.e., a particular antidote is frequently suitable only for use with individual species of cultivated plants and/or for protecting the cultivated plants from individual herbicidal substances or classes of substances.

U.S. Pat. No. 5,858,924 describes certain [1,2,4]triazolo[1,5-c]pyrimidin-2-yl)-arylbenzenesulfonamide compounds and their use as herbicides. While certain of these compounds have been shown to be particularly effective herbicides for controlling undesirable vegetation in water-seeded, direct-seeded and transplanted paddy rice, they have also been shown to produce slight amounts of damage to the rice at concentrations required to adequately control the undesirable vegetation.

SUMMARY OF THE INVENTION

Surprisingly, it has now been found that, the phytotoxic effect on rice of penoxsulam can be ameliorated by the use of clomazone, a rice herbicide in its own right with a different mode of action. The present invention concerns a composition for protecting water-seeded, direct seeded and transplanted paddy rice from the harmful effects of penoxsulam and its agriculturally acceptable salt derivatives which comprises, in addition to the penoxsulam, clomazone as a safener. The present invention also concerns a method of protecting water-seeded, direct-seeded and transplanted paddy rice from the harmful effects of penoxsulam and its agriculturally acceptable salt derivatives which comprises contacting the water-seeded, direct-seeded and transplanted paddy rice with, or applying to the area under cultivation, clomazone as a safener.

DETAILED DESCRIPTION OF THE INVENTION

Penoxsulam is the common name for 2-(2,2-difluoroethoxy)-N-(5,8-dimethoxy[1,2,4]triazolo[1,5-c]pyrimidin-2-yl)-6-(trifluoromethyl)benzene-sulfonamide Its herbicidal activity is described in *The Pesticide Manual*, Fourteenth Edition, 2006. Penoxsulam controls annual grass weeds, broadleaf weeds, and sedge weeds in rice, but can demonstrate some phytotoxicity to rice under certain conditions of rates, water flooding, timing of application, and rice varieties.

Clomazone is the common name for 2-[(2-chlorophenyl)methyl]-4,4-dimethyl-3-isoxazolidinone. Its herbicidal activity is described in *The Pesticide Manual*, Fourteenth Edition, 2006. Clomazone controls a wide range of grass weeds in rice and certain broadleaf crops.

The term herbicide is used herein to mean an active ingredient that kills, controls or otherwise adversely modifies the growth of unwanted plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation. The term safener, as used herein, refers to a compound or compounds that selectively protects crop plants from herbicide damage without significantly reducing activity in target weed species.

Herbicidal activity is exhibited by the compounds when they are applied directly to the plant or to the locus of the plant via foliar, soil, or water application at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, paddy water quality and depth, and the like, as well as the amount of chemical applied. These and other factors can be adjusted as is known in the art to promote non-selective or selective herbicidal action. Generally, it is preferred to apply the composition of the present invention to relatively immature undesirable vegetation to achieve the maximum control of weeds.

Cultivated plants which are to be protected from the adverse effect of undesirable plant growth may be damaged to a certain degree when an effective dose of herbicide is used. Safening means preventing the adverse effect of an herbicide on the cultivated plants, i.e., protecting the cultivated plants without, at the same time, noticeably influencing the herbicidal action on weeds to be combated.

In the composition of this invention, the weight ratio of penoxsulam to clomazone at which the herbicidal effect on the cultivated plant is safened lies within the range of between about 1:2 and about 1:100, preferably in the range of between about 1:5 and about 1:20.

The rate at which the safened composition is applied will depend upon the particular type of weed to be controlled, the degree of control required, and the timing and method of application. In general, the composition of the invention can be applied at an application rate of between about 5 to 60 grams per hectare (g/ha) of penoxsulam and about 100 to 650 g/ha of clomazone in the composition, respectively. In an especially preferred embodiment of the invention, clomazone is applied at a rate between about 220 g/ha and about 450 g/ha and penoxsulam is applied at a rate of about 40 g/ha.

The penoxsulam and clomazone used in the present invention can be applied either separately or together as part of a multipart herbicidal system.

The herbicide-safener mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the rice herbicides that can be employed in conjunction with the safened composition of the present invention include: 2,4-D esters and amines, 2,4-MCPA, acetochlor, acifluorfen, aclonifen, AE0172747, alachlor, amidosulfuron, aminopyralid, aminotriazole, ammonium thiocyanate, anilifos, azimsulfuron, benfuresate, bensulfuron-methyl, bentazone, benthiocarb, benzobicyclon, bifenox, bispyribac-sodium, butachlor, butafenacil, butralin, cafenstrole, carbetamide, carfentrazone-ethyl, chlorflurenol, chlorimuron, cinosulfuron, clethodim, clopyralid, cloransulam-methyl, cyclosulfamuron, cycloxydim, cyhalofop-butyl, dicamba, dichlobenil, dichlorprop-P, diclosulam, diflufenican, diflufenzopyr, dimethenamid, dimethenamid-p, diquat, dithiopyr, diuron, EK2612, EPTC, esprocarb, ET-751, ethoxysulfuron, ethbenzanid, F7967, fenoxaprop, fenoxaprop-ethyl, fenoxaprop-ethyl+isoxidifen-ethyl, fentrazamide, flazasulfuron, florasulam, fluazifop, fluazifop-P-butyl, flucetosulfuron, flufenacet, flufenpyr-ethyl, flumetsulam, flumiclorac-pentyl, flumioxazin, fluometuron, flupyrsulfuron, fluroxypyr, fluroxypyr esters and salts, fomesafen, foramsulfuron, fumiclorac, glufosinate, glufosinate-ammonium, glyphosate, halosulfuron, haloxyfop-methyl, haloxyfop-R, HOK-201, imazamethabenz, imazamox, imazapic, imazapyr, imazaquin, imazethapyr, imazosulfuron, indanofan, indaziflam, iodosulfuron, ioxynil, IR 5790, isoproturon, isoxaben, isoxaflutole, KUH-071, lactofen, linuron, MCPA, MCPA ester & amine, mecoprop-P, mefenacet, mesosulfuron, mesotrione, metamifop, metolachlor, metosulam, metribuzin, metsulfuron, molinate, MSMA, napropamide, NC-620, nicosulfuron, norflurazon, OK-9701, orthosulfamuron, oryzalin, oxadiargyl, oxadiazon, oxazichlomefone, oxyfluorfen, paraquat, pendimethalin, pentoxazone, pethoxamid, picloram, picolinafen, piperophos, pretilachlor, profoxydim, propachlor, propanil, propyzamide, prosulfocarb, prosulfuron, pyraclonil, pyrazogyl, pyrazosulfuron, pyribenzoxim, pyriftalid, pyrimisulfan (KUH-021), pyriminobac-methyl, primisulfuron, propyrisulfuron (TH-547), pyroxsulam, pyroxasulfone (KIH-485), quinclorac, quizalofop-ethyl-D, S-3252, saflufenacil, sethoxydim, SL-0401, SL-0402, s-metolachlor, sulcotrione, sulfentrazone, sulfosate, tebuthiuron, tefuryltrione (AVH-301), thiazopyr, thiobencarb, triclopyr, triclopyr esters and amine, and tritosulfuron.

It is generally preferred to use the herbicide-safener mixture of the present invention in combination with herbicides that are selective for the crop being treated and which complement the spectrum of weeds controlled by these compounds at the application rate employed. It is further generally preferred to apply the safened composition of the present invention and other complementary herbicides at the same time, either as a combination formulation or as a tank mix.

In practice, it is preferable to use the safened composition of the present invention in mixtures containing an herbicidally effective amount of the herbicidal components along with at least one agriculturally acceptable adjuvant or carrier. The carrier can be water, soil, sand, a fertilizer granule, a clay granule, a paper/cellulose granule, or other materials that can serve as a physical carrier of the safened composition. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, sand, soil, dusts, granules, water dispersible granules, or wettable powders, or liquids, such as, for example, emulsifiable concentrates, solutions, emulsions, suspensions or water.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual", MC Publishing Corp., Ridgewood, N.J., 1998 and in "Encyclopedia of Surfactants", Vol. I-III, Chemical publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; and esters of the above vegetable oils.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicide-safener mixture of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, by hand, by addition to paddy or irrigation water, and by other conventional means known to those skilled in the art.

The following examples illustrate the present invention.

Evaluation of Postemergence Herbicidal Safening in Water-Seeded Rice

Pre-germinated rice was applied directly into a flooded rice paddy. The rice paddy was prepared as per normal cultural practices, by applying appropriate fertilizers, working and leveling the ground before flooding, with water flooded across the entire field to a depth of 1 to 5 inches prior to seeding with the pre-germinated rice seed.

Treatments consisted of penoxsulam and clomazone applied alone and in combination directly into the flooded rice paddy as granular formulated treatments. These treatments could also be applied as liquid applications directly into the water. Clomazone was applied the day of rice seeding, at 13 days after rice seeding, and in combination with penoxsulam at 13 days after rice seeding. Penoxsulam was applied alone and in combination with clomazone at 13 days after rice seeding.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected} = A + B - (A \times B / 100)$$

A = observed efficacy of active ingredient A at the same concentration as used in the mixture.

B = observed efficacy of active ingredient B at the same concentration as used in the mixture.

Some of the safener-herbicide combinations tested, application rates and ratios employed, plant species tested, and results are given in Tables 1-3.

Evaluation of Herbicidal Safening in Water-Seeded Rice

Tables 1 and 2 demonstrate the safening activity of clomazone on the rice injury from an application of penoxsulam directly into the water of water-seeded rice. Table 1 demonstrates that penoxsulam applied at 40 g ai/ha at 13 days after rice seeding caused slight injury to rice at 7, 14 and 21 days after application, with % visual injury declining over time. Clomazone applied at the same time (13 days after seeding) to water-seeded rice caused slight (0-3%) visual injury to rice. When both penoxsulam and clomazone were applied at the same time at 13 days after seeding, rice injury was significantly reduced due to the safening effect of clomazone on the penoxsulam injury to the water-seeded rice. As the rate of clomazone increased, the safening effect to penoxsulam injury on the rice also increased as noted by reducing visual injury ratings.

Table 2 demonstrates the same safening effect of clomazone on penoxsulam injury to the rice stand or to the population of rice plants per unit area. Again, as seen in the % visual injury ratings seen in Table 1, clomazone had a safening effect on the impact of penoxsulam on the rice stand. Penoxsulam had a slight negative impact on the rice stand, and clomazone had a negligible effect on the rice stand. When penoxsulam and clomazone were applied at the same time at 13 days after the rice seeding, the rice stand was significantly improved compared to the penoxsulam alone treatment.

Evaluation of Herbicidal Activity in Water-Seeded Rice

The results presented in Table 3 demonstrate that, with respect to weed control of ECHOR, LEFFA and CYPDI, clomazone did not antagonize or reduce the activity of penoxsulam on these three weeds.

TABLE 1

Rice % Visual Injury

| Application Rate (g ai/ha) | | Days After Seeding | Rice % Visual Injury Ratings (%) | | | | | |
|---|---|---|---|---|---|---|---|---|
| | | | ORYSA (1) | | ORYSA (2) | | ORYSA (3) | |
| Penoxsulam | Clomazone | | Obs | Exp | Obs | Exp | Obs | Exp |
| 40 | 0 | 13 | 12 | — | 9 | — | 5 | — |
| 0 | 224 | 13 | 0 | — | 1 | — | 0 | — |
| 0 | 336 | 13 | 2 | — | 3 | — | 3 | — |
| 0 | 448 | 13 | 3 | — | 1 | — | 0 | — |
| 40 | 224 | 13 | 7 | 12 | 6 | 10 | 4 | 5 |
| 40 | 336 | 13 | 5 | 14 | 4 | 12 | 2 | 8 |
| 40 | 448 | 13 | 3 | 15 | 3 | 10 | 3 | 5 |
| 0 | 0 | 13 | 0 | 0 | 0 | 0 | 0 | 0 |

(1) % Visual rice injury at 7 days after treatment.
(2) % Visual rice injury at 14 days after treatment.
(3) % Visual rice injury at 21 days after treatment.
ORYSA = *Oryza sativa* 'M205' (rice)
Obs = observed values
Exp = expected, calculated values
g ai/ha = gram active ingredient per hectare

TABLE 2

Rice % Stand Reduction

| Application Rate (g ai/ha) | | Days After Seeding | Rice % Stand Reduction Ratings (%) | | | | | |
|---|---|---|---|---|---|---|---|---|
| | | | ORYSA (1) | | ORYSA (2) | | ORYSA (3) | |
| Penoxsulam | Clomazone | | Obs | Exp | Obs | Exp | Obs | Exp |
| 40 | 0 | 13 | 27 | 27 | 33 | 33 | 33 | 33 |
| 0 | 224 | 13 | 2 | 2 | 0 | 0 | 3 | 3 |
| 0 | 336 | 13 | 7 | 7 | 2 | 2 | 3 | 3 |
| 0 | 448 | 13 | 8 | 8 | 3 | 3 | 3 | 3 |
| 40 | 224 | 13 | 17 | 29 | 23 | 33 | 18 | 36 |
| 40 | 336 | 13 | 13 | 34 | 17 | 35 | 13 | 36 |
| 40 | 448 | 13 | 17 | 35 | 19 | 36 | 12 | 36 |
| 0 | 0 | 13 | 0 | 0 | 1 | 1 | 2 | 2 |

(1) % Visual rice stand reduction at 7 days after treatment.
(2) % Visual rice stand reduction at 14 days after treatment.
(3) % Visual rice stand reduction at 28 days after treatment.
ORYSA = *Oryza sativa* 'M205' (rice)
Obs = observed values
Exp = expected, calculated values
g ai/ha = gram active ingredient per hectare

TABLE 3

% Weed Control

| Application Rate (g ai/ha) | | Days After Seeding | % Weed Control Ratings (%) | | | | | |
|---|---|---|---|---|---|---|---|---|
| | | | ECHOR (1) | | LEFFA (2) | | CYPDI (3) | |
| Penoxsulam | Clomazone | | Obs | Exp | Obs | Exp | Obs | Exp |
| 40 | 0 | 13 | 98 | — | 74 | — | 99 | — |
| 0 | 224 | 13 | 93 | — | 98 | — | 73 | — |
| 0 | 336 | 13 | 96 | — | 99 | — | 88 | — |
| 0 | 448 | 13 | 97 | — | 99 | — | 87 | — |
| 40 | 224 | 13 | 99 | 99 | 96 | 99 | 99 | 99 |
| 40 | 336 | 13 | 98 | 99 | 99 | 99 | 99 | 99 |
| 40 | 448 | 13 | 99 | 99 | 99 | 99 | 99 | 99 |
| 0 | 0 | 13 | 0 | 0 | 0 | 0 | 0 | 0 |

(1) % Visual Weed Control of ECHOR at 27 days after treatment.
(2) % Visual Weed Control of LEFFA at 27 days after treatment.
(3) % Visual Weed Control of CYPDI at 27 days after treatment.
ECHOR = *Echinochloa oryzoides* (watergrass)
LEFFA = *Leptochloa fascicularis* (sprangletop)
CYPDI = *Cyperus difformis* (smallflower umbrella sedge)
Obs = observed values
Exp = expected, calculated values
g ai/ha = gram active ingredient per hectare

What is claimed is:

1. A method of protecting water-seeded, and transplanted paddy rice from the harmful effects of penoxsulam and its agriculturally acceptable salt derivatives which comprises applying directly into the water of the water-seeded, or transplanted paddy rice, clomazone as a safener.

2. The method of claim 1 in which the penoxsulam is applied after the seeding or transplanting of the rice and the clomazone is applied either at the time of seeding or transplanting the rice or at the same time as the penoxsulam is applied.

* * * * *